(12) United States Patent
Gilliam et al.

(10) Patent No.: US 8,871,062 B2
(45) Date of Patent: Oct. 28, 2014

(54) FALLING FILM EVAPORATOR

(76) Inventors: Charles David Gilliam, Baton Rouge, LA (US); Stefanie Renee Gilliam, Baton Rouge, LA (US)

(*) Notice: Subject to any disclaimer, the term of this patent is extended or adjusted under 35 U.S.C. 154(b) by 607 days.

(21) Appl. No.: 12/953,058

(22) Filed: Nov. 23, 2010

(65) Prior Publication Data

US 2012/0129242 A1    May 24, 2012

(51) Int. Cl.
| | |
|---|---|
| *B01D 1/22* | (2006.01) |
| *B01D 3/28* | (2006.01) |
| *C02F 1/08* | (2006.01) |
| *F15D 1/00* | (2006.01) |
| *C12N 1/12* | (2006.01) |

(52) U.S. Cl.
CPC . *B01D 1/221* (2013.01); *C02F 1/08* (2013.01); *C12N 1/12* (2013.01); *Y10S 203/11* (2013.01); *Y10S 165/914* (2013.01)
USPC ............... 203/1; 159/13.2; 159/27.1; 159/44; 159/49; 202/236; 203/10; 203/89; 203/100; 137/2; 137/561 R; 210/86; 210/87; 210/252; 165/115; 165/914

(58) Field of Classification Search
USPC ........... 159/13.1, 13.2, 27.1, 44, 49; 165/115, 165/914; 202/236; 203/10, 72, 89, 100, 1; 137/561 R, 2; 210/86, 87, 252
See application file for complete search history.

(56) References Cited

U.S. PATENT DOCUMENTS

| | | | | |
|---|---|---|---|---|
| 2,545,028 | A | * | 3/1951 | Haldeman ...................... 261/153 |
| 3,175,962 | A | * | 3/1965 | Holtslag ........................ 202/236 |
| 3,199,574 | A | * | 8/1965 | Keller ............................. 159/6.2 |

(Continued)

OTHER PUBLICATIONS

Schenk, Peer M., et al; "Second Generation Biofuels: High-Efficiency Microalgae for Biodiesel Production"; Bioenerg. Res. (2008) 1:20-43.
Melis, Anastasios, et al; "Hydrogen Production. Green Algae as a Source of Energy"; Plant Physiology, Nov. 2001, vol. 127, pp. 740-748.
Brennan, Liam, et al; "Biofuels from microalgae—A review of technologies for production, processing, and extractions of biofuels and co-products"; (2009), doi: 10.1016/j.rser.2009.10.009.
Benemann, John R.; "Biofixation of CO2 and Greenhouse Gas Abatement with Microalgae-Technology Roadmap"; Final Report Submitted to the U.S. Department of Energy National Energy Technology Laboratory and Steering Committee of the International Network n Biofixation of CO2 and Greenhouse Gas Abatement with Microalgae; Jan. 14, 2003; pp. 1-29.

*Primary Examiner* — Virginia Manoharan
(74) *Attorney, Agent, or Firm* — Roy Kiesel Ford Doody & Thurmon, APLC (57) ABSTRACT

An apparatus and method are disclosed for controlling the thickness of a flowing, laminar fluid film. The film flow may be gravity-induced or the result of an alternative force. The fluid is deposited on an upper end of a flow surface where a relatively thick layer of the film forms. The film flows over a fluid dispersal region where the surface area is rapidly expanding, which results in rapid thinning of the film thickness. The fluid then flows over an active region where the surface area is designed to control the fluid film thickness. For example, in some applications, it may be desirable to maintain an approximately constant film thickness as the fluid flows over the active region of the surface. The geometry of the flow surface is used to obtain the desired control over the fluid film thickness. The flow surface is the outer surface of a solid with a closed upper end and a lower end that may be open or closed. An open lower end allows for injection of a heated material, which may be used to heat the solid surface. This process may be used to heat the fluid flow surface so that evaporation of the flowing fluid results. A falling film evaporator is one application of the disclosed invention. A carbon capture system using a thin, flowing algae film is another application. Other potential uses of the invention are disclosed as well.

16 Claims, 5 Drawing Sheets

(56) References Cited

U.S. PATENT DOCUMENTS

| | | | | |
|---|---|---|---|---|
| 3,271,969 | A | * | 9/1966 | Lorentzen ............ 62/98 |
| 3,500,893 | A | * | 3/1970 | McReynolds ............ 159/13.3 |
| 3,788,954 | A | * | 1/1974 | Cantrell ............ 203/89 |
| 4,706,741 | A | * | 11/1987 | Bolmstedt et al. ............ 165/115 |
| 5,453,158 | A | * | 9/1995 | Cummings et al. ............ 159/47.1 |
| 5,792,663 | A | * | 8/1998 | Fry et al. ............ 436/73 |
| 7,258,767 | B2 | * | 8/2007 | Ter Beek et al. ............ 203/10 |
| 7,785,448 | B2 | * | 8/2010 | Owens ............ 203/10 |
| 2007/0048848 | A1 | | 3/2007 | Sears |
| 2010/0160673 | A1 | * | 6/2010 | Bruns et al. ............ 560/347 |
| 2011/0178734 | A1 | * | 7/2011 | Clerico et al. ............ 702/45 |
| 2013/0055755 | A1 | * | 3/2013 | Kompa ............ 62/515 |

OTHER PUBLICATIONS

Kratz, William A., et al; "Photosynthesis and Respiration of Three Blue-Green Algae"; Department of Zoology, University of Texas, Austin 12, Texas, pp. 275-280; Jan. 19, 1955.

Peng, Ching-An, "Amelioration of Greenhouse Effect in Southern California: Carbon Dioxide Sequestration by Algae"; Southern California Studies Center University of Southern California; pp. 1-10; Apr. 15, 1999.

\* cited by examiner

FIG. 6

FALLING FILM EVAPORATOR

FIELD OF THE INVENTION

The present invention relates to a falling film evaporation, and more generally to a solid, flowing fluid film surface configured to manipulate and control the thickness of the fluid film flowing over the surface. The invention further relates to a method of controlling the thickness of a fluid film flowing over a solid surface.

BACKGROUND OF THE INVENTION

A variety of devices has been constructed to create a thin flowing laminar fluid film. Falling film evaporators are a common example. An evaporator is a device designed to convert a liquid into a gas. Evaporation may be desired for various reasons, including for the distillation or purification of a liquid such as water. Seawater may be converted into potable water using evaporative technology, and this application is particularly important given the growing demand for potable water.

In a falling film evaporator, contaminated liquid is supplied to generally vertical heat exchange tubes. For example, in a seawater purification evaporator of this type, the seawater is the input. Seawater flows down vertical tubes while heat—typically in the form of steam—is supplied to the area outside the tubes. By allowing only a thin film of seawater to flow down the tubes, the heat transferred to the water is sufficient to evaporate some of the water. This water vapor, which is now pure water, rises up the center part of the tube. The vapor is then collected in some fashion and condensed to produce pure water.

Falling film evaporators work best when the flowing film thickness is maintained at a desired thickness. Returning to the seawater evaporator example, a relatively thin film is desired so that maximum evaporation will occur. If the film is too thick, evaporation will be inhibited. If the film is too thin, all the water will evaporate, leaving the tube surface dry. The latter situation can be damaging because of the combination of the high temperature tube surface with the various salts and other contaminants left behind by the evaporation. Hard scale deposits can result, and such scale can be effectively baked onto the tubes. This scale can be hard to remove, can reduce the heat transfer capability of the tubes, and can cause localized tube corrosion, particularly where the deposited materials are corrosive. For this reason, it is important to prevent drying of the tube surfaces in a falling film seawater evaporator.

One means used to avoid drying of the tube surface is to increase the flow rate of the fluid. By flowing more seawater down the tubes, there is less risk of the tubes drying. However, this also means the film layer will be thicker, which tends to reduce the evaporation rate. To offset this reduced thermal efficiency, a seawater falling film evaporator may employ a higher temperature. That is, rather than heating the tubes to 140° F., which is considered an optimal temperature for evaporation without significant scale adhesion to the heat transfer surface, an evaporator using higher seawater flow rates may need to raise the temperature substantially above this point. That increased heating will produce more evaporation, but it also will result in more baked on scale on the tubes. These trade offs render the falling film evaporator much less desirable as a means for purifying seawater.

In some applications, it may be desirable to evaporate the flowing fluid quickly within a particular region of the apparatus. For example, some liquids may contain certain entrained or dissolved gasses with relatively low flash points. It may be desired to selectively evaporate off these materials so that each can be separately handled. This operation is difficult to achieve in a conventional falling film evaporator. To achieve this result, long tubes may be needed and separate heating regions used along the tubes.

A somewhat new use of flowing film technology involves use of thin films of algae to capture carbon dioxide from the atmosphere. Algae use light and carbon dioxide to create energy, oxygen, and other products. Algae have been identified as a potentially important means of capturing carbon, that is, by removing carbon dioxide from the air.

In a falling film algae carbon capture apparatus, a thin film of algae may flow through an area exposed to light. Carbon dioxide rich air may be fed into the apparatus in the lighted region. The carbon dioxide is consumed by the algae which then flows past the lighted region and is further processed to remove any desired by products of the operation. For this process to work well, it is important to have the algae at a warm temperature, and that means some evaporation will occur. It is also desirable to maintain the algae at a constant film thickness to better facilitate the carbon capture.

These potential uses of falling film technology and the inherent trade offs presented by the use of a falling film evaporator to purify seawater or other contaminated liquids identify an important need. There is a need for an improved falling film apparatus and method that will obtain the potential benefits without the undesirable consequences. The present invention provides just such an apparatus and method.

SUMMARY OF THE INVENTION

The present invention provides a geometric solution to the problems noted above. A member is disclosed the serves the function of the falling film evaporator tube briefly described above. This member, however, is not an open-ended tube. It is closed on one end, that is, on the upper end in a vertical application. The liquid is deposited on the closed end and then flows down the outside surface of the member. The second end of this member, which is the lower end in a vertical application, may be open or closed. If open, the second end may allow the injection of a heated fluid into an inner chamber, thus heating the surface of the member. This operation is different from the typical falling film evaporator, which supplies heat to the area outside the tubes. In the present invention, if heat is supplied, it is supplied to the inside of the fluid flow member. The fluid to be processed flows down the outside of the member, not down the inside of a tube.

The present invention employs at least two distinct fluid flow regions: a fluid dispersal region and an active region. The fluid dispersal region has a rapidly expanding surface area. This geometric configuration results in rapid thinning of the fluid layer deposited on the top of the member. Once the fluid film thickness has reached the desired thickness, the fluid dispersal region ends.

The active region begins after the fluid dispersal region, though a transition or other region could be positioned between the fluid dispersal region and active region. Once in the active region, the fluid film thickness is controlled to achieve the desired result. In a seawater purification use, the fluid film would be maintained approximately constant. To achieve this result without altering the overall flow rate, the surface area of the active region may be decreased. That is, with some of the water evaporating off the surface in the active region, the film layer will get thinner unless the surface area is decreasing. By matching the rate of decrease in the surface area to the rate of evaporation, a generally constant fluid film thickness may be maintained. This allows for efficient heat transfer at optimum temperatures (e.g., about 140° F.). It prevents drying of the heat transfer surface, too.

If, on the other hand, it is desired to evaporate off certain components separately, then multiple dispersal and active regions could be used. Different heating levels also could be employed toward this end. The present invention provides sufficient flexibility to allow for these types of variations.

DETAILED DESCRIPTION

Figure 1:
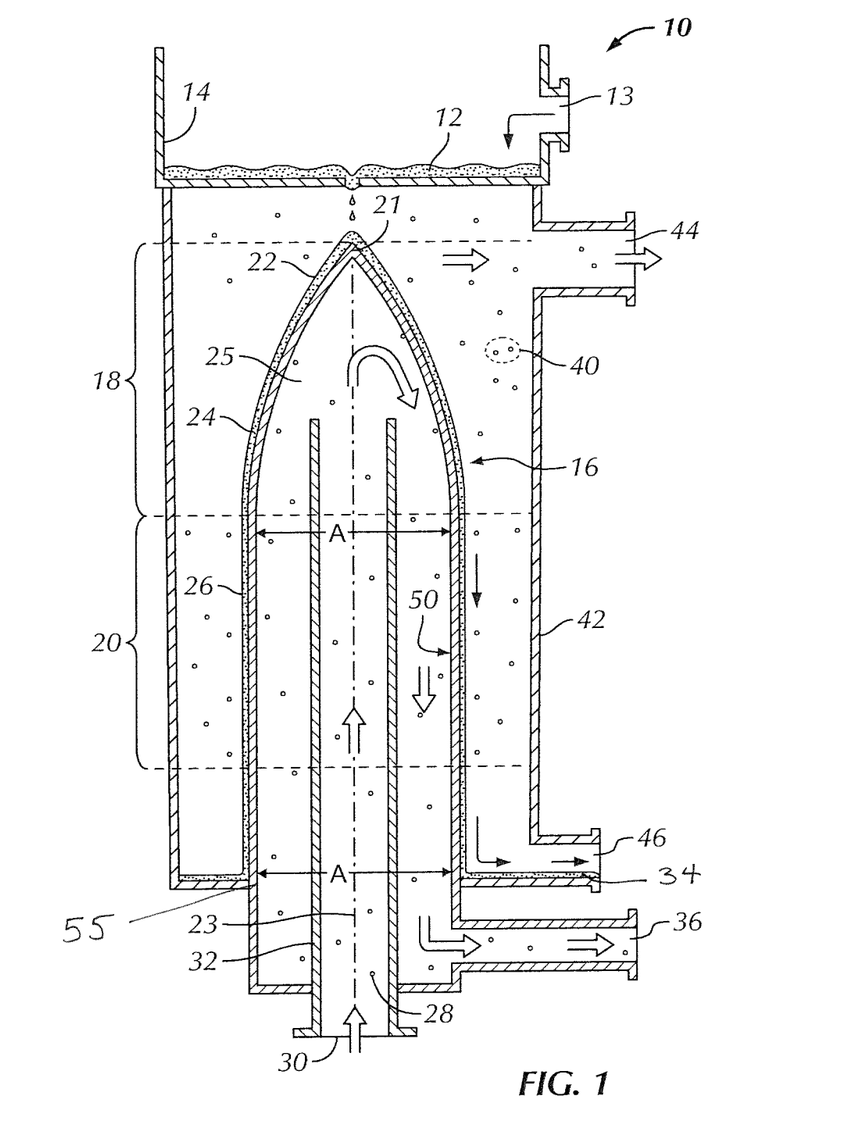
FIG. 1 is a cross-sectional view of a preferred embodiment of the present invention.

One expected use of the present invention is as a falling film evaporator. Such an evaporator is shown in cross-sectional view in FIG. 1. This embodiment of the invention may not be the most desired configuration for the purification of contaminated water, such as seawater. The embodiment shown in FIG. 1 is, however, an accurate representation of certain general characteristics of the present invention. FIG. 1, therefore, will be used to explain the basic structure and operation of the present invention.

A falling film evaporator 10 is shown in FIG. 1. Contaminated input liquid 12 is shown in an upper feed trough 14. A feed inlet 13 is shown, too, though the supply liquid can be provided in various ways. For example, rather than the dripping trough structure shown in FIG. 1, and inlet feed pipe or tube could be used, with its outlet positioned near the point where the liquid is shown dripping out of the trough 14. The structure and method used to supply the liquid to the apparatus is not central to the present invention.

A fluid flow member 16 is shown in the central area of FIG. 1. This member, and in particular, the variably curved surface of this member, represent key aspects of the invention. The fluid flow member 16 is separated into two important regions, a fluid dispersal region 18 and an active region 20. The liquid is quickly dispersed in the fluid dispersal region 18. That is, the fluid film thickness is quickly reduced in this region. The active region, on the other hand, is the region where maximum evaporation occurs, or where other activity occurs if the invention is not employed in an evaporator.

As the contaminated liquid 12 drips onto the upper area 21 of the fluid dispersal region 18, a relatively thick film layer is formed. The upper area 21 shown in FIG. 1 comes to a somewhat sharp point. In most actual embodiments of the present invention, it is expected that the upper area 21 would be less sharp or pointed than is shown in FIG. 1. Indeed, a relatively flat upper area 21 may be desirable in some applications. The slope of the curve of the outer member surface within the fluid dispersal region is dependent upon the nature of the fluid.

When water or other relatively thin liquids are used, a curvature such as that shown in FIG. 1 may be desirable. The desired outcome is a fluid film thickness that works best within the active region. With a water purification evaporator, for example, the fluid film with thin quickly. But if a thicker fluid is used, a much different curvature may be needed in the fluid dispersal region. An outer surface curve that is relatively flat at the top 21 will provide and highest rate of increase in surface area with decrease in elevation. In other words, a flatter upper area 21 will allow the fluid film to thin more with a given decrease in elevation. This may be needed for thicker fluids.

A parabolic curve is one preferred curvature for the outer surface of the fluid dispersal region 18. To generate the shape, a parabola is rotated around the vertical central axis 23. The central longitudinal axis 23 extends from the center of the upper end 21 to a point at the center of the generally cylindrical lower end 55. The shape of the fluid dispersal region 18 can be varied depending upon the specific parabola, or other type of curve, used. For thick fluids, a parabola with a flatter upper region would be desired, but for thinner fluids like water, a curve similar to that shown in FIG. 1 may be desirable. The present invention allows the designer to vary this aspect of the invention to best suit the particular needs of the application.

One possible application where a flatter upper end 21 may be desired would be the concentration of syrup, molasses, liquid malt extract, or other thick, sticky liquids. Such liquids flow slowly unless heated. By flowing such a liquid down the member 16 of the present invention, and allowing evaporation within the active region 20, the product may be substantially concentrated. This process may reduce the volume of weight of the material, thus allowing for easier storage or shipping. These applications of the invention are provided to show a specific situation in which a different curvature for the outer surface of the fluid dispersal region 18 might be desired.

A relatively thick layer of fluid 22 is shown near the upper end 21. As the fluid flows through the fluid dispersal region 18 it thins. A thinner film layer 24 is shown near the lower end of the fluid dispersal region 18. This is the film thickness as the fluid enters the active region 20. An active film thickness 26 is shown within the active region 20. In FIG. 1, this film thickness 26 is shown as approximately constant within the active region 20. That result is shown for illustration purposes only, because a different geometry is needed in the active region 20 to achieve that result in an evaporator. Fluid that did not evaporate 34, is collected at the lower end of the structure and exhausted from the apparatus by outlet 46.

Evaporated vapor 40 leaves the outer surface of the member 16, with most evaporation occurring within the active region 20. The vapor 40 rises and is removed from the apparatus through outlet 44. The outer housing 42 shown in FIG. 1 is illustrative only, as any suitable housing may be used. In fact, in a practical embodiment of the present invention, there may be multiple members 16 constructed as a group. In this variation, the contaminated or concentrated liquid outlet 46 and the water vapor outlet 44 may be common to multiple members 16.

Within the member 16, there may be heated fluid inlet tube 32 with an inlet 30 and an outlet 36. Steam 28 is shown flowing up the tube 32 and then down to the outlet 36. As the steam flows back down, it is exposed to the inner surface 50 of the member 16. The surface of the member 16 is heated in this manner, and may thus evaporate some of the fluid flowing down the surface.

The member 16 is closed at the top (i.e., the area in which the liquid is initially deposited), and the lower end 55 is shown open in FIG. 1. An open lower end 55 allows heat to be supplied to the member 16. The lower end 55, however, may be closed if there is not need for external heat. Whether the lower end 55 is open or closed, an inner chamber 25 is formed.

The inner chamber 25, of course, is only accessible if the lower end 55 is open.

The active region 20 is generally cylindrical, and is shown in FIG. 1 with a generally constant radius. This geometry is represented by the same diameters A shown at the upper and lower ends of the active region 20 in FIG. 1. As will be explained below, the invention uses different geometries for the active region 20 to achieve different results for the fluid film.

The arrows used in FIGS. 1-4 show the flow paths of the different fluids. Using FIG. 1 for illustrative purposes, the single-line arrows represent liquids, while the double-line arrows represent gases. The liquid feed enters through inlet 13, as shown by the arrow. A similar, single-line arrow shows the flow of the liquid down the outside surface of member 16 and then out the outlet 46. Evaporation of some of the liquid produces water vapor 40, which rises and then exits the device through vapor outlet 44, as shown by the double-line arrows. Steam used to supply heat to the device is shown with double-line arrows within the inner chamber 25. Steam 28 is shown flowing up the tube 32 (by double-line arrows) and then down to the outlet 36 (again represented by the double-line arrows). The same arrow arrangement is used in other figures to represent the flow of fluids within the device.

Figure 2:
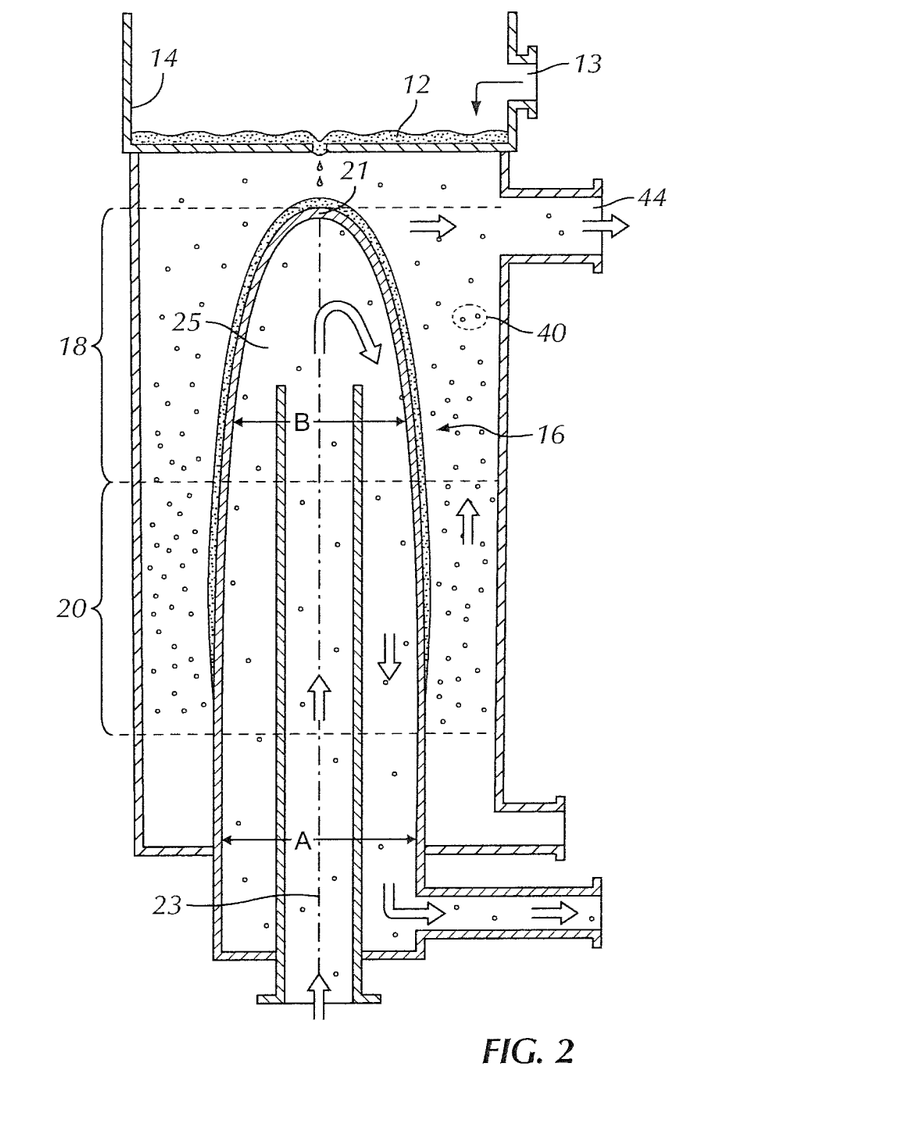
FIG. 2 is a cross-sectional view of an alternative preferred embodiment of the present invention.
Figure 3:
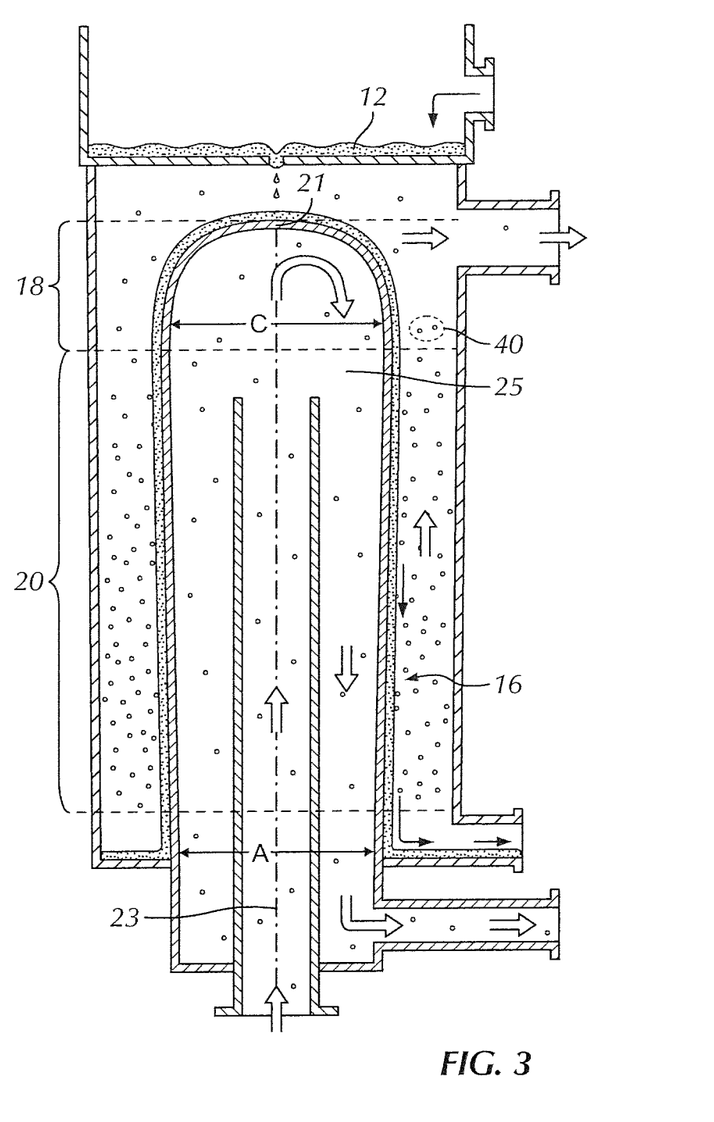
FIG. 3 is a cross-sectional view of an alternative preferred embodiment of the present invention.

FIGS. 2 and 3 show important variations on the embodiment shown in FIG. 1. Each of these figures shows a different curvature in both the fluid dispersal region 18 and the active region 20. FIG. 2, for example, shows a flatter upper end 21 in the fluid dispersal region 18. This curvature will give fluids more time to thin as the fluids flow down the member 16.

The active region 20 in FIG. 2 is significantly different from the active region 20 of FIG. 1. In FIG. 1, the active region 20 has a relatively constant cross sectional area. That is, in FIG. 1, the active region 20 is generally cylindrical, with the diameters represented by A and B being approximately equal. Diameter A represents the diameter of the lower end of the active region 20. Diameter B, on the other hand, shows the diameter of the upper end of the active region 20, that is, of the point where the fluid dispersal region 18 ends and the active region 20 begins. In FIG. 1, diameters A and B are roughly equal, and the outer surface area within the active region 20 is not increasing or decreased as one moves along the longitudinal axis 23.

In FIG. 2, however, the active region 20 is quite different. Diameter A is now larger than diameter B. In other words, the upper part of the active region 20 in FIG. 2 has less surface area than the lower part. The surface area is increasing in the active region 20 in the direction of flow (i.e., downward). The rate of increase of the surface area within the active region 20, however, is less than the rate of increase in surface area within the fluid dispersal region 18.

This different configuration produces markedly different results. The same inner chamber 25 is shown in FIG. 2 and steam is supplied to that chamber 25 to heat the member 16, just as in FIG. 1. The heated surface results in evaporation, thus removing some of the liquid from the surface. Because the surface area is increasing and the amount of fluid remaining on the surface is decreasing, the fluid film thickness will continue to decrease in the active region 20 of FIG. 2. This result is illustrated by the vapor 40 ending some distance above the lower end of the member 16, and by the complete elimination of the film layer at a point above the lower end of the member 16.

The flow path arrows helps show this dynamic. Liquid is fed into the trough 14 through the inlet 13, as shown by the single-line arrow. Double-line arrows show the gaseous form of the material evaporating from the outer surface of the member 16. Note that no liquid lines are shown leaving the lower end of the device in FIG. 2, because all the liquid is evaporated in this embodiment.

The complete evaporation of the feed liquid may be undesirable in some applications, such as seawater purification systems. Nevertheless, it may be desirable in other contexts. If for example, it were desired to completely evaporate the entire liquid being supplied to the apparatus, using the configuration shown in FIG. 2 would greatly enhance the chances of achieving this outcome. FIG. 2 shows how the curvature of the surface of the active region 20 can be used to substantially vary the performance of the apparatus.

FIG. 3 shows another variation, and this one may be more suitable for a seawater purification system. In this embodiment, the upper end 21 of the fluid dispersal region 18 is relatively flat. This allows for rapid thinning of the fluid film thickness. It also allows for more of the length of the element 16 to be used for evaporation, which may be desirable.

The active region 20 shown in FIG. 3 has a decreasing surface area in the downward direction along the longitudinal axis 23. This can be seen by the difference in the diameters A and C. Diameter A is at the lower end of the active region 20, and it is shown to be approximately the same diameter as that shown in FIGS. 1 and 2. Diameter C, on the other hand, is at the upper end of the active region 20, near the point where the active region 20 meets the fluid dispersal region 18. Diameter C is larger than diameter A, meaning that the outer surface area of the active region 20 is decreasing as the fluid flows downward.

The embodiment shown in FIG. 3 may be suitable for a seawater purification system. By decreasing the surface area with decreasing elevation within the active region 20, an approximately constant fluid film thickness may be achieved. As in FIGS. 1 and 2, vapor 40 is shown evaporating from the fluid as is flows through the active region 20. If the surface area decreases at the same rate as fluid evaporates from the fluid film, a constant film thickness may be achieved. This is a highly desirable result because it prevents drying of the surface (i.e., and thus reduces scale build-up) and allows for maximum thermal efficiency.

Figure 4:
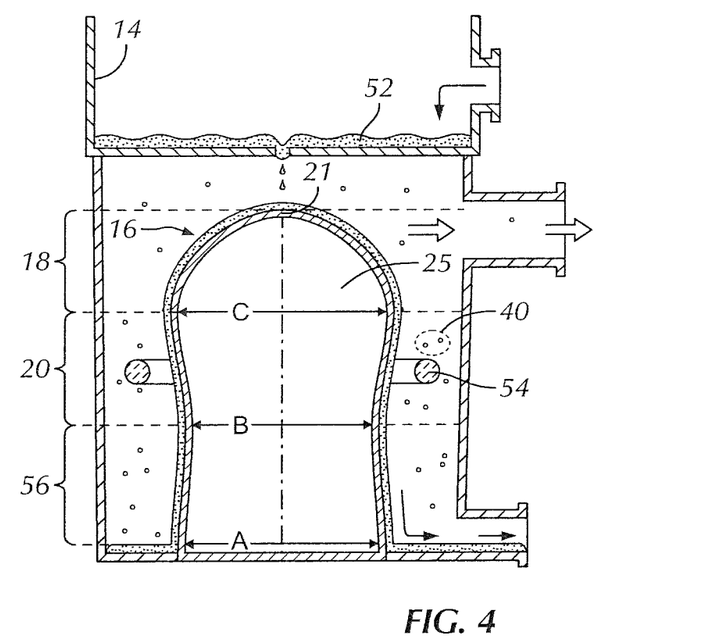
FIG. 4 is a cross-sectional view of an alternative preferred embodiment of the present invention.
Figure 5:
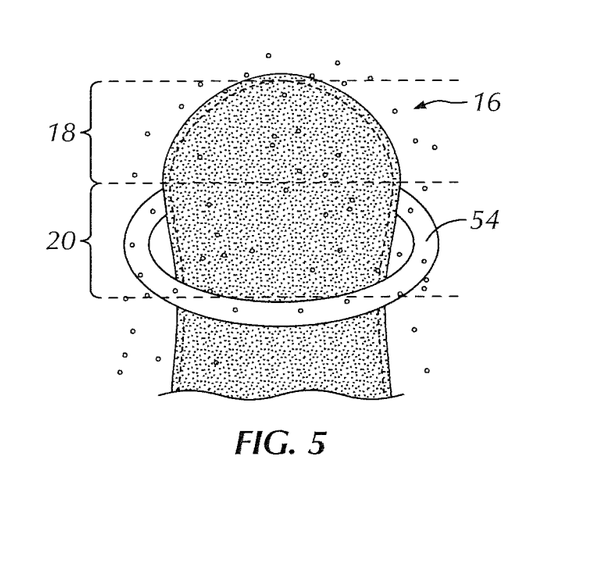
FIG. 5 is a perspective view of the embodiment of FIG. 4.

FIGS. 4 and 5 show the invention used in an algae-based carbon capture apparatus. The member 16 is shown with a closed upper and lower end. This may be desired in this embodiment for simplicity of design and because there may not be a need for a means of heating the inner chamber 25. Algae 52 are shown in the feed trough 14. The algae are deposited on the upper end 21 of the fluid dispersal region 18, where the algae 52 thin to a layer thickness appropriate for carbon capture.

The active region 20 in FIG. 4 is that area in proximity to the light source 54, shown as a light ring in cross section in FIG. 4. Some evaporation 40 may occur, but it may be desirable to minimize evaporation in this embodiment.

The member 16 shown in FIG. 4 has three distinct regions. The fluid dispersal region 18 and active region 20 are present, as in prior drawings. In FIG. 4, the active region is somewhat similar to that shown in FIG. 3. That is, the surface area decreases in the active area in the direction (i.e., downward) of the algae flow. This accounts for some evaporation, while keeping the algae film at a generally constant thickness. If no evaporation is expected, the active region 20 for this embodiment may be shaped like that shown in FIG. 1.

The third region in FIG. 4 is a recovery region 56. In this region, the algae cease functioning because they are too far from the light source. The algae flow though the recovery region 56 and are then collected for further use. A recovery region 56 as shown in FIG. 4 may be included in any embodiment of the invention, but may be less desirable is space is at a premium. For example, in a water purification system, it may be desirable to use as much of the member 16 as possible for heat transfer and evaporation, thus increasing the productivity of the apparatus.

FIG. 5 is a perspective view of the carbon capture apparatus of FIG. 4. The fluid dispersal region 18 and active region 20 are shown, with the light ring 54 surrounding the active region 20. The member 16 is shown in FIG. 5 without any housing or other structure. This illustration is provided to give a perspective image of the invention.

Figure 6:
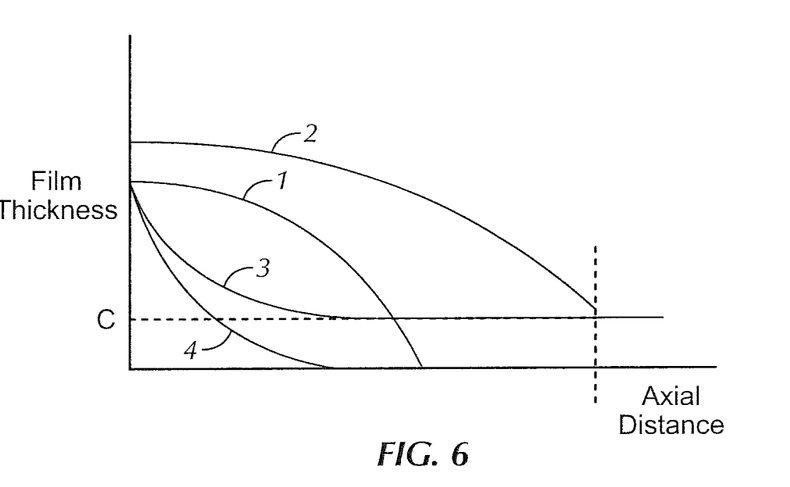
FIG. 6 is an illustration of the fluid film thickness profiles of various embodiments of the present invention.

FIG. 6 is a series of curves that illustrate the performance of the invention with different geometries. Curve 1 shows possible performance of an embodiment like that shown in FIG. 1. The upper end 21 of the fluid dispersal region 18 of FIG. 1 has a relatively sharp point. This shape will allow the fluid to flow downward without a great deal of thinning. This result is illustrated in FIG. 6 by the relatively flat section at the start of Curve 1. In this part of Curve 1, the film thickness decreases rather slowly with axial distance (i.e., with decrease in elevation for a vertically oriented member 16). The film thickness begins to decrease more rapidly as the distance increases because of evaporation. If there is sufficient evaporation, or insufficient flow rate, the film thickness may decrease to zero, as shown for Curve 1.

There are ways to prevent the film thickness from decreasing to zero in the embodiment represented by Curve 1. Either the flow rate may be increased, the heat input may be decreased, or a combination of the two. If these changes are made, it is possible to maintain flow along the entire length of member 16, as is shown in Curve 2. This curve, however, represents suboptimal evaporation (i.e., because the fluid film is thicker) and, therefore, may not be a desirable result.

Curve 3 shows the result of the embodiment shown in FIG. 3. The flatter upper end 21 of the fluid dispersal region 18 results in a rapid thinning of the fluid layer thickness, as shown in Curve 3. The film thickness decreases until it reaches a constant level, denoted by the constant C. This film thickness is maintained by decreasing the surface area of the active region 20 in proportion to the evaporative losses, as explained above in connection with FIG. 3.

Curve 4 shows the result of using the embodiment of FIG. 2. A relatively flat upper end 21 is used, thus producing rapid reduction of the film thickness in the fluid dispersal region. But the film thickness continues to decrease in Curve 4 because the surface area continues to increase in the active region 20 of the embodiment shown in FIG. 2. This results in the film thickness being reduced to zero, quite possibly at a point relatively far up the length of the member 16. This result is illustrated by Curve 4 of FIG. 6.

While the preceding description is intended to provide an understanding of the present invention, it is to be understood that the present invention is not limited to the disclosed embodiments. To the contrary, the present invention is intended to cover modifications and variations on the structure and methods described above and all other equivalent arrangements that are within the scope and spirit of the following claims.

We claim:

1. A fluid flow member, comprising
A. a closed first end;
B. a second end having a generally cylindrical cross section, wherein a central longitudinal axis is defined by a line extending from a center point of the closed first end to a point at the center of the generally cylindrical cross section of the second end, and wherein the second end is open, thus forming an inner chamber accessible via the second end;
C. a variably curved outer flow surface extending from the closed first end to the second end, the surface having two fluid flow regions, namely,
  i. a fluid dispersal region extending from the first end to a point between the first end and second end, the fluid dispersal region being defined by a surface curvature that produces an increasing surface area as the region extends from the first end toward the second end along the central longitudinal axis; and,
  ii. an active region extending from a point below the fluid dispersal region, the active region having an increasing surface area as the region extends along the central longitudinal axis in a direction away from the fluid dispersal region and toward the second end, and wherein the rate of increase of the surface area in the active region is less than the rate of increase of the surface area in the fluid dispersal region.

2. A fluid flow member, comprising
A. a closed first end;
B. a second end having a generally cylindrical cross section, wherein a central longitudinal axis is defined by a line extending from a center point of the closed first end to a point at the center of the generally cylindrical cross section of the second end, and wherein the second end is open, thus forming an inner chamber accessible via the second end;
C. a variably curved outer flow surface extending from the closed first end to the second end, the surface having two fluid flow regions, namely,
  i. a fluid dispersal region extending from the first end to a point between the first end and second end, the fluid dispersal region being defined by a surface curvature that produces an increasing surface area as the region extends from the first end toward the second end along the central longitudinal axis; and,
  ii. an active region extending from a point below the fluid dispersal region, the active region having a decreasing surface area as the region extends along the central longitudinal axis in a direction away from the fluid dispersal region and toward the second end and wherein the rate of decrease in the active region surface area is selected to maintain an approximately constant fluid film thickness within the active region.

3. The member of claim 2, wherein the rate of decrease in the active region surface area is matched to an evaporation rate of the fluid as it flows through the active region.

4. The member of claim 2, wherein the inner chamber is configured to receive heat.

5. The member of claim 4, wherein a curvature of the outer surface of the active region is selected to maintain an approximately constant film thickness when the inner chamber is heated sufficiently to produce substantial evaporation of the fluid flowing over the surface of the active region.

6. The member of claim 5, wherein the curvature of the outer surface of the active region is selected to maintain an approximately constant film thickness when a liquid consisting primarily of water flows over the surface of the action region having a surface temperature of approximately 140° F.

7. The member of claim 4, wherein the inner chamber is configured to receive a heated fluid.

8. The member of claim 7, wherein the inner chamber further comprises a heated fluid supply tube and a heated fluid outlet.

9. The member of claim 2, wherein the curvature of the outer surface of the fluid dispersal region is defined geometrically by the rotation of a generally parabolic curve around the central longitudinal axis.

10. The member of claim 9, wherein the generally parabolic curve is selected to provide a rapidly expanding surface area in the section of the fluid dispersal region nearest the closed first end of the member.

11. The member of claim 10, wherein the generally parabolic curve is selected to produce a desired fluid film thickness at the beginning of the active region.

12. A falling film evaporator comprising:

A. a liquid inlet;

B. a generally vertical evaporation member having a closed first end, an open second end, a variably curved outer surface and an inner surface, wherein, i. the inner surface is configured to received a heated fluid via the open second end; and, ii. the outer surface has two fluid flow regions, namely, a. a fluid dispersal region beginning near an upper end of the member and extending in a generally downward direction; and, b. an active region extending in a generally downward direction from a point below the fluid dispersal region, the active region having a surface curvature with a decreasing surface area as the region extends along the central longitudinal axis in a direction away from the fluid dispersal region and toward the second end wherein the rate of decrease in the active region surface area is selected to maintain an approximately constant fluid film thickness within the active region.

13. The evaporator of claim 12, wherein the outer surface is maintained at approximately 140° F. within the active region.

14. The evaporator of claim 12, wherein the active region has a decreasing horizontal cross sectional area that decreases at a rate matched to an evaporation rate of fluid within the active region.

15. A method of controlling laminar fluid flow over a surface, comprising:

A. depositing a fluid on the surface such that laminar flow of the fluid results;

B. rapidly thinning the laminar fluid flow layer by flowing the fluid over a fluid dispersal region of the surface, wherein the fluid dispersal region has an increasing surface area in the direction of the fluid flow; and, C. flowing the fluid over an active region of the surface, wherein the active region has a decreasing surface area as the region extends along a central longitudinal axis in a direction away from the fluid dispersal region; and, D. controlling the laminar fluid flow layer thickness within the active region to achieve a desired result.

16. The method of claim 15, wherein the desired result is to maintain an approximately constant laminar fluid layer thickness across the active region in an environment where some of the flowing fluid is evaporating from the surface.

* * * * *